(12) United States Patent
Michael et al.

(10) Patent No.: US 8,666,234 B1
(45) Date of Patent: Mar. 4, 2014

(54) FILM MOUNTED AROMA DEVICE

(76) Inventors: Daryl A. Michael, Newton, IA (US); Jennifer L. Michael, Newton, IA (US)

( * ) Notice: Subject to any disclaimer, the term of this patent is extended or adjusted under 35 U.S.C. 154(b) by 456 days.

(21) Appl. No.: 11/956,401

(22) Filed: Dec. 14, 2007

Related U.S. Application Data

(63) Continuation of application No. 11/467,285, filed on Aug. 25, 2006, now abandoned.

(51) Int. Cl.
*A61L 9/03* (2006.01)
*A61L 9/12* (2006.01)
*A61L 9/04* (2006.01)
*B32B 33/00* (2006.01)

(52) U.S. Cl.
USPC ............. 392/386; 239/34; 239/57; 239/60; 428/41.8; 428/905

(58) Field of Classification Search
USPC .......... 239/34–60, 6; 392/386–406; 424/123–125, 118; 428/41.8, 905; 40/593, 594
See application file for complete search history.

(56) References Cited

U.S. PATENT DOCUMENTS

| | | | | |
|---|---|---|---|---|
| 3,274,706 | A * | 9/1966 | Friend | 434/295 |
| 3,568,356 | A * | 3/1971 | Berman | 446/118 |
| 4,482,799 | A * | 11/1984 | Pricenski et al. | 392/388 |
| 4,528,226 | A * | 7/1985 | Sweeny | 428/40.2 |
| 4,749,222 | A | 6/1988 | Idland | |
| 4,824,707 | A * | 4/1989 | Spector | 428/46 |
| 4,900,604 | A * | 2/1990 | Martinez et al. | 428/79 |
| 5,447,439 | A * | 9/1995 | Nathanson | 434/346 |
| 5,471,773 | A | 12/1995 | Hoffman | |
| 5,525,177 | A | 6/1996 | Ross | |
| 5,533,289 | A | 7/1996 | Hoffman | |
| 5,574,821 | A * | 11/1996 | Babasade | 392/392 |
| 5,577,947 | A * | 11/1996 | Malloy et al. | 446/220 |
| 5,609,938 | A | 3/1997 | Shields | |
| 5,830,529 | A | 11/1998 | Ross | |
| 5,887,118 | A * | 3/1999 | Huffman et al. | 392/390 |
| 6,258,200 | B1 | 7/2001 | Kassab | |
| 6,361,752 | B1 * | 3/2002 | Demarest et al. | 422/306 |
| 6,672,748 | B2 | 1/2004 | Baldwin | |
| 6,775,470 | B2 * | 8/2004 | Zobele et al. | 392/390 |
| 7,065,910 | B2 * | 6/2006 | Woodruff | 40/544 |
| 7,137,570 | B2 * | 11/2006 | Wheatley et al. | 239/32 |
| 7,188,783 | B2 * | 3/2007 | Ivey et al. | 239/136 |
| 2004/0161572 | A1 * | 8/2004 | Juran et al. | 428/41.8 |
| 2006/0196964 | A1 * | 9/2006 | Wheatley et al. | 239/57 |
| 2007/0160809 | A1 * | 7/2007 | Juran et al. | 428/138 |

OTHER PUBLICATIONS http://www.geocities.com/ugotemel/toys/a_sugar.htm,"Sugar & Spice" date unknown.*

* cited by examiner

*Primary Examiner* — Darren W Gorman
(74) *Attorney, Agent, or Firm* — Ryan N. Carter

(57) ABSTRACT

An aroma dispensing device includes a flexible film having opposite first and second sides, with the first side having a releasable agent to removably adhere the film to a surface. An aroma source is mounted to the second side of the film for dispensing a fragrance to an area adjacent the surface. The film adheres by static cling or an adhesive which does not leave a residue on the surface when the film is removed. The device may include an activator for actuating dispensement of the fragrance from the aroma source, as well as a power source for actuating a fan and providing power to the activator.

16 Claims, 2 Drawing Sheets

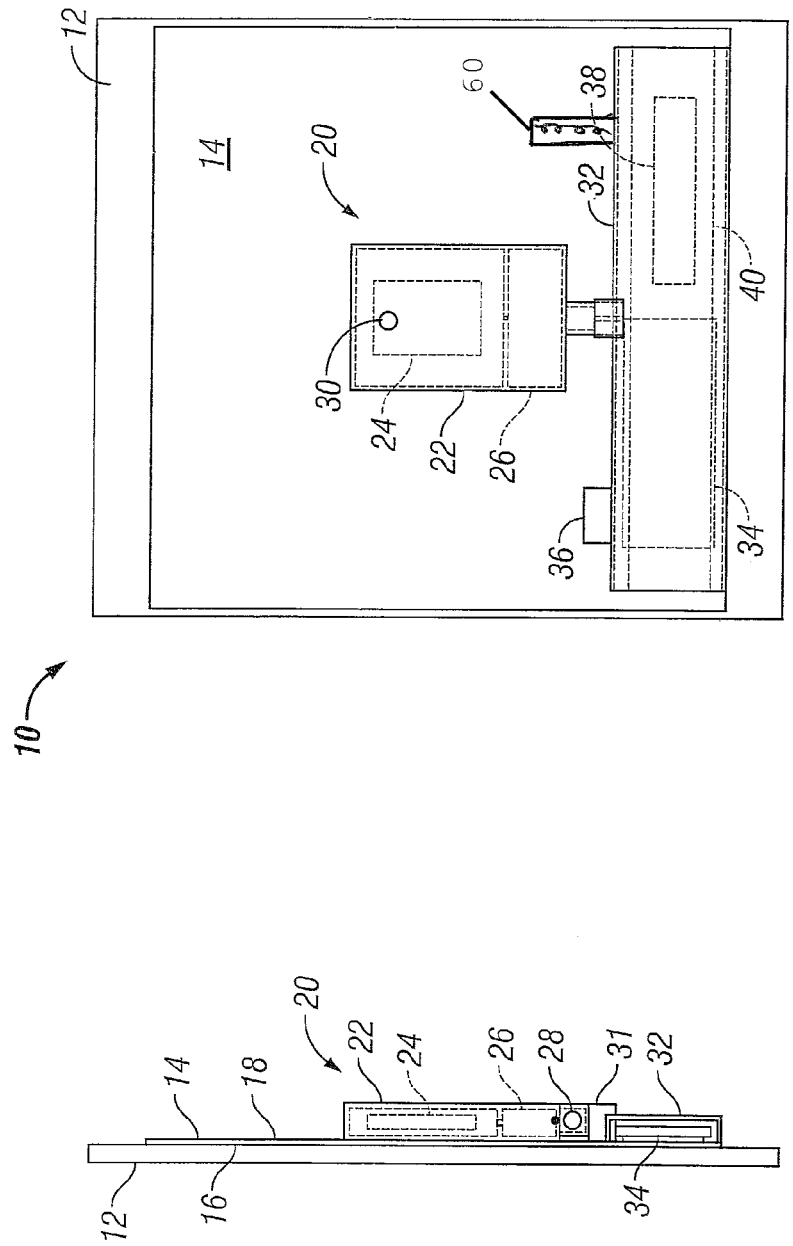

FILM MOUNTED AROMA DEVICE

CROSS-REFERENCE TO RELATED APPLICATIONS

This application is a Continuation Application of U.S. Ser. No. 11/467,285 filed Aug. 25, 2006, herein incorporated by reference in its entirety.

BACKGROUND OF THE INVENTION

1. Field of the Invention

The present invention relates to releasably-mounted aroma dispensers, and more particularly to an aroma dispenser mounted on a thin, flexible film which adheres to a surface, such as glass, using static cling or residue-free adhesive.

2. Description of the Prior Art

Visual displays are known in the prior art which mount to a window or other smooth surface using a film having electrostatic adherence, or static cling to the surface. For example, see U.S. Pat. Nos. 5,533,289; 5,609,938; 6,258,200; 6,672,748; and 7,065,910. These devices typically are mounted on one side of a window for viewing by a person on the other side of the window. The film has an image thereon for advertising, promotion, or other communication. In other applications, the film is adhered to a smooth, opaque surface so that the image is viewable from the same side of the surface. Some prior art devices include a light source powered by a solar cell or battery to illuminate the image for easier viewing. Some prior art devices also include a rigid frame, which makes it difficult to mount the device to a surface which is curved or irregular.

All of these prior art display devices are limited to visual images, and do not provide stimulation to other senses, such as smell.

Accordingly, a primary objective of the present invention is the provision of an aroma dispensing device which is removably adhered to a surface.

Another objective of the present invention is the provision of an aroma dispensing device which is mounted on a flexible film for use on smooth surfaces, including glass, ceramic, plastic, and metal.

Another objective of the present invention is the provision of an aroma dispensing device mounted on a flexible film for adherence to flat and curved smooth surfaces.

Still another objective of the present invention is the provision of an aroma dispensing device which can be mounted to a surface using static cling.

Yet another objective of the present invention is the provision of an aroma dispensing device secured to a flexible film which can be removably adhered to a smooth surface using electrostatic attraction.

A further objective of the present invention is the provision of an aroma dispensing device mounted on flexible film which can be adhered to a surface using an adhesive which does not leave a residue when the film is removed from the surface.

Still another objective of the present invention is the provision of an aroma dispensing device mounted on a window or other surface and activated by heat, light, moisture, motion, electric current, unsealing, and/or a timer.

A further objective of the present invention is an aroma dispensing device mounted on a flexible film with a fan to blow a fragrance from the device.

Yet another objective of the present invention is the provision of an aroma dispensing device having a fan mounted on a film, with the fan being powered by a battery, a rechargeable cell, photovoltaic or an alternating current supply.

Another objective of the present invention is the provision of a film-mounted aroma dispensing device having multiple scent packs for a user to select different fragrances.

Yet another objective of the present invention is the provision of an aroma dispensing device mounted on a flexible film and having a circuit board on the film to control dispensement of the fragrance.

Another objective of the present invention is the provision of an aroma dispensing device mounted on a film and having a pump on the film to dispense fragrance from the device.

Still another objective of the present invention is the provision of an aroma dispensing device on a flexible film which also dispenses a chemical to eliminate odors.

Another objective of the present invention is the method of dispensing a fragrance from an aroma source mounted on a flexible film removably adhered to a surface.

These and other objectives will become apparent from the following description of the invention.

BRIEF SUMMARY OF THE INVENTION

The aroma dispensing device of the present invention includes a flexible film having opposite first and second sides, with the first side having a releasable adherent to removably adhere the film to a smooth, flat or curved surface. The releasable agent may be static cling or an adhesive which does not leave a residue when the film is removed from the surface. An aroma source is mounted on the film for dispensing a fragrance into the area adjacent the surface to which the film is mounted.

An activator may be provided on the film to activate the aroma source. The activator may include heat, light, moisture, or a removable seal. A power source may also be included on the film to operate a fan to blow the fragrance away from the film. The power source may be a battery, an alternating current, a rechargeable cell, or a photovoltaic. A time may also be provided with the activator to periodically release the aroma at pre-selected times. Multiple scent packs may be provided on the film for a user to select a desired fragrance. The device may also include a pump, with an inlet and an outlet to facilitate the dispensement of aroma from the device. The device may also dispense a chemical to eliminate odors.

The method of fragrance dispensement according to the present invention includes the step of removably adhering a flexible film to a surface, and activating an aroma source on the film to dispense a fragrance from the aroma source.

BRIEF DESCRIPTION OF THE DRAWINGS

FIG. 1 is a side elevation view of one embodiment of the aroma dispensing device of the present invention, mounted on a surface.

FIG. 2 is a rear elevation view of the device of FIG. 1.

DETAILED DESCRIPTION OF THE PREFERRED EMBODIMENT

Figure 4:
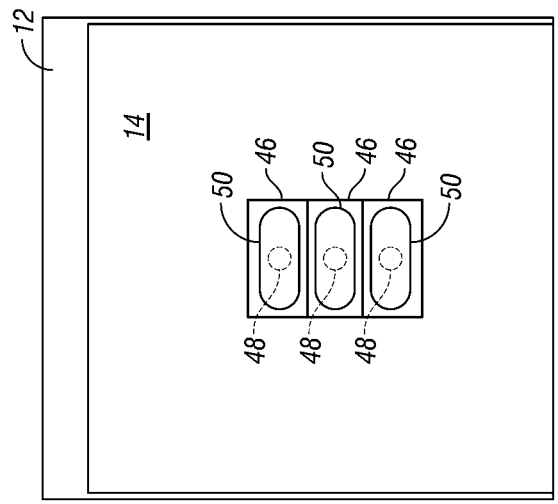
FIG. 4 is a rear elevation view of another alternative embodiment of the aroma dispensing device having multiple scent packs.

The aroma display device of the present invention is generally designated by the reference numeral 10 in the drawings. Device 10 is shown to be mounted on a surface 12, such as a window, glass, ceramic, plastic, or metal. While the drawings show the surface 12 to be flat, it is understood that the device 10 can be applied to any relatively smooth surface, including a curved surface.

The device 10 includes a flexible film 14 with opposite first and second sides 16, 18. The first or front side 16 of the film 14 is adapted to adhere to the surface 12 using static cling, or using an adhesive which will not leave a residue on the surface 12 when the film 14 is removed from the surface 12. The static cling or residue-free adhesive allows the film 14 to be quickly and easily mounted on the surface 12, and removed from the surface 12 as desired. One example of the adhesive is an acrylic copolymer, such as that used on Post-It® notes, and described in U.S. Pat. No. 3,691,140.

The device 10 further includes an aroma assembly 20 mounted on the second, or rear side 18 of the film 14. The aroma assembly 20 includes housing 22 with an aroma source therein. In one embodiment shown in FIGS. 1 and 2, a pressure chamber 26 is provided in the housing 22, with an air inlet valve 28 communicating with the pressure chamber 26, and an air outlet valve 30 communicating with the aroma source 24. Piezoelectric pump 31 is provided on the aroma assembly 20 for pressurizing the chamber 26 to facilitate the dispensement of a fragrance from the aroma source 24 through the outlet valve 30. The inlet valve 28 and outlet valve 30 are normally closed.

A second housing 32 is provided on the aroma assembly 20 for enclosing a circuit board 34 used to control the dispensement of a fragrance from the aroma source 24. An activator 36 may also be provided on or in the housing 32 so as to activate the dispensement of fragrance from the aroma source 24. The activator may take numerous forms. For example, the activator 36 may apply heat to the pressure chamber 26 to increase the air pressure therein. Alternatively, the activator 36 may apply heat directly to the aroma source 24, in the absence of a pressure chamber 26. The activator may also generate a fragrance from the aroma source 24 through the application of light. As a further alternative, the activator 36 may supply moisture to the aroma source 24, which activates the dispensement of fragrance there from. As a further alternative, the activator 36 may include a motion detector, such that when an individual enters the area where the device 10 is mounted, a fragrance is emitted. As still another alternative, a timer may be provided on the activator 36 so as to dispense a fragrance at a predetermined time or intervals.

Figure 3:
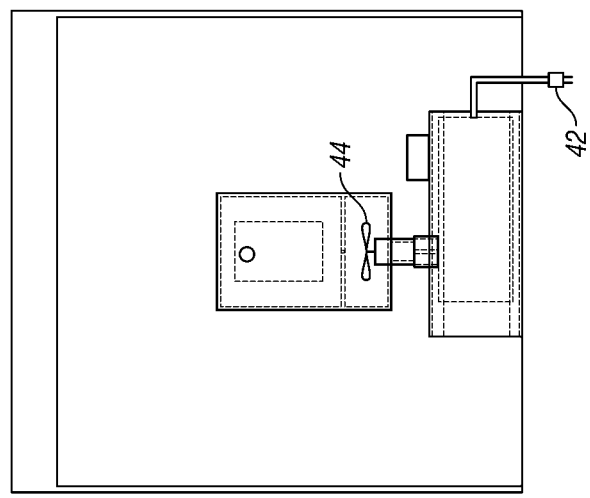
FIG. 3 is a rear elevation view of an alternative embodiment of the aroma dispensing device according to the present invention.

The aroma assembly 20 also includes a power source, which may take several forms. For example, the power source may be a battery 38 or other rechargeable cell, coupled to a photovoltaic 40. Alternatively, the power source may be a hard wire and plug 42 for connection to an AC outlet, as seen in FIG. 3. The power source can be used to drive a fan 44, a resistive element, or the piezoelectric pump 31 so as to disperse the aromatic fragrance.

In another embodiment, the aroma assembly 20 may simply be a housing with one or more scent packets 46 therein. Outlet openings 48 may be associated with each scent packet 46 with a removable seal 50 normally covering the outlets 48. A person can then select one or more of the scent packets 46 simply by removing the seal or seals 50, which allows air to circulate past the scent packet so as to dispense a fragrance there from.

In an embodiment without a power source, the aroma source may be an aromatic paraffin, gel, or scented film simply mounted to the substrate film 14 so as to supply a fragrance to the area adjacent the surface 12 to which the film 14 is applied.

As another alternative, the device 10 may be provided with indicia representing the fragrance being dispersed. For example, if the device 10 is emitting a citric scent, the indicia may include the image of an orange or the word "orange".

With the flexibility of the film 14, the device 10 can be mounted for various applications, including in showers, bathroom stalls, or pet caddies. In a shower, the device may include an open cell foam treated with the aromatic scent such that moisture from the shower activates the device for release of the scent.

The device 10 may also include a chemical mounted within the housing 22 which can be dispensed in the same manner as the fragrance so as to eliminate odors.

The device 10 may also include a night light 60 operatively connected to the power source. Switches may also be provided with the device to allow a user to turn the device 10 on and off, and allow the user to adjust the output levels or to select different fragrances from the multiple scent packs 46.

It is understood that the housings 22 and 32 may be integrated into a single housing unit, as opposed to separate housings.

The film 14 can be printed with decorative graphics to enhance the visual appeal of the sound device 10. The device 10 can also include a sound generating device, such as described in Applicant's co-pending application Ser. No. 11/467,260, filed on Aug. 25, 2006 entitled FILM MOUNTED SOUND DEVICE", incorporated herein by reference. The sound device 10 may also be coupled with a dynamic display, as described in Applicant's co-pending application Ser. No. 11/467,271, filed on Aug. 25, 2006, entitled FILM MOUNTED DYNAMIC DISPLAY DEVICE, incorporated by reference herein.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:
1. An aroma dispensing device, comprising:
a flexible static cling film having opposite first and second sides, the first side removably adhering the film to a surface by static cling;
an aroma source mounted to the second side of the film for dispensing a fragrance to an area adjacent the surface; and
an aroma activator mounted on the second side of the film and connected to the aroma source to activate the aroma source only after the film is adhered to the surface;
wherein the activator supplies heat to the aroma source.
2. An aroma dispensing device, comprising:
a flexible static cling film having opposite first and second sides, the first side removably adhering the film to a surface by static cling;
an aroma source mounted to the second side of the film for dispensing a fragrance to an area adjacent the surface; and
an aroma activator mounted on the second side of the film and connected to the aroma source to activate the aroma source only after the film is adhered to the surface;
wherein the activator supplies light to the aroma source.
3. An aroma dispensing device, comprising:
a flexible static cling film having opposite first and second sides, the first side removably adhering the film to a surface by static cling;

an aroma source mounted to the second side of the film for dispensing a fragrance to an area adjacent the surface; and
an aroma activator mounted on the second side of the film and connected to the aroma source to activate the aroma source only after the film is adhered to the surface;
wherein the activator supplies moisture to the aroma source.

4. An aroma dispensing device, comprising:
a flexible static cling film having opposite first and second sides, the first side removably adhering the film to a surface by static cling;
an aroma source mounted to the second side of the film for dispensing a fragrance to an area adjacent the surface; and
an aroma activator mounted on the second side of the film and connected to the aroma source to activate the aroma source only after the film is adhered to the surface;
wherein the activator senses motion to activate the aroma source.

5. An aroma dispensing device, comprising:
a flexible static cling film having opposite first and second sides, the first side removably adhering the film to a surface by static cling;
an aroma source mounted to the second side of the film for dispensing a fragrance to an area adjacent the surface; and
an aroma activator mounted on the second side of the film and connected to the aroma source to activate the aroma source only after the film is adhered to the surface;
wherein the activator supplies an electric current to the aroma source.

6. An aroma dispensing device, comprising:
a flexible static cling film having opposite first and second sides, the first side removably adhering the film to a surface by static cling;
an aroma source mounted to the second side of the film for dispensing a fragrance to an area adjacent the surface; and
an aroma activator mounted on the second side of the film and connected to the aroma source to activate the aroma source only after the film is adhered to the surface;
wherein the activator includes a timer mounted on the film to activate the aroma source at a pre-selected time.

7. An aroma dispensing device, comprising:
a flexible static cling film having opposite first and second sides, the first side removably adhering the film to a surface by static cling;
an aroma source mounted to the second side of the film for dispensing a fragrance to an area adjacent the surface; and
an aroma activator mounted on the second side of the film and connected to the aroma source to activate the aroma source only after the film is adhered to the surface;
further comprising an aroma power source connected to the film to dispense the fragrance.

8. The aroma dispensing device of claim 7 wherein the power source includes a battery.

9. The aroma dispensing device of claim 7 wherein the power source is connectable to an AC outlet.

10. The aroma dispensing device of claim 7 wherein the power source includes a rechargeable cell.

11. The aroma dispensing device of claim 7 wherein the power source includes a photovoltaic.

12. An aroma dispensing device, comprising:
a flexible static cling film having opposite first and second sides, the first side removably adhering the film to a surface by static cling;
an aroma source mounted to the second side of the film for dispensing a fragrance to an area adjacent the surface; and
an aroma activator mounted on the second side of the film and connected to the aroma source to activate the aroma source only after the film is adhered to the surface;
further comprising a light mounted on the film.

13. An aroma dispensing device, comprising:
a flexible static cling film having opposite first and second sides, the first side removably adhering the film to a surface by static cling;
an aroma source mounted to the second side of the film for dispensing a fragrance to an area adjacent the surface; and
an aroma activator mounted on the second side of the film and connected to the aroma source to activate the aroma source only after the film is adhered to the surface;
further comprising a fan mounted on the film to blow the fragrance away from the film.

14. An aroma dispensing device, comprising:
a flexible static cling film having opposite first and second sides, the first side removably adhering the film to a surface by static cling;
an aroma source mounted to the second side of the film for dispensing a fragrance to an area adjacent the surface; and
an aroma activator mounted on the second side of the film and connected to the aroma source to activate the aroma source only after the film is adhered to the surface;
further comprising a pump to dispense the fragrance.

15. An aroma dispensing device, comprising:
a flexible static cling film having opposite first and second sides, the first side removably adhering the film to a surface by static cling;
an aroma source mounted to the second side of the film for dispensing a fragrance to an area adjacent the surface; and
an aroma activator mounted on the second side of the film and connected to the aroma source to activate the aroma source only after the film is adhered to the surface;
wherein the activator includes a circuit board on the film to control dispensement of the fragrance.

16. An aroma dispensing device, comprising:
a flexible static cling film having opposite first and second sides, the first side removably adhering the film to a surface by static cling;
an aroma source mounted to the second side of the film for dispensing a fragrance to an area adjacent the surface; and
an aroma activator powered by an electrical power source and mounted on the second side of the film and connected to the aroma source to activate the aroma source only after the film is adhered to the surface.

* * * * *